United States Patent [19]

DeMil

[11] Patent Number: 4,797,151

[45] Date of Patent: Jan. 10, 1989

[54] PROCESS FOR IMPROVING FLORAL FERTILITY

[76] Inventor: Edmond A. DeMil, 140 rue Saint-Charles, 75015 Paris, France

[21] Appl. No.: 908,404

[22] Filed: Sep. 16, 1986

[30] Foreign Application Priority Data

Sep. 17, 1985 [FR] France .................. 85 13738

[51] Int. Cl.$^4$ .......................................... A01N 37/02
[52] U.S. Cl. ....................................................... 71/113
[58] Field of Search ........................................ 71/113

[56] References Cited

FOREIGN PATENT DOCUMENTS 240302H 8/1977 France .

Primary Examiner—Catherine L. Mills
Attorney, Agent, or Firm—Lucas & Just

[57] ABSTRACT

Improved floral fertility is obtained by applying lipoaminoacids to plants during the period between floral induction and the end of inflorescence of the plant. Foliar spraying can be used to apply a solution or aqueous suspension that has 10 to 1000 ppm of lipoaminoacids. The solution of suspension is applied in amounts of 5 to 100 g per hectare.

5 Claims, No Drawings

PROCESS FOR IMPROVING FLORAL FERTILITY

It is well known that floral abortion is, presently, an important problem in the agricultural field: a high floral abortion rate results in poor production yields with all the corresponding economic consequences. If such problem could be partially solved, it would result in a more regular agricultural production.

The studies of J.C. VALLEE [Thése Nov. 1972, Faculté des Sciences de Dijon, "Quelques aspects du métabolisme de la proline sur les divers nicotiana en fonction du développement"], of E. Perdrizet, J. C. Vallee, C. Martin, [(1967) Comptes-rendus, Académie des Sciences, Série D, 264, 1024–1027, (1968) Comptes-rendus, Annales physiologie Vég., 10, 237–250, (1969) Comptes-rendus, Académie des Sciences, Série D, 269, 1190–1193], and also of Margara, Bouniols et alii [(1971) Comptes-rendus, Académie des Sciences Paris, Série D, 273, 1104–1107 and 1193–1196] demonstrated, in laboratory, that sugar and salt could have some action on the floral induction and that phenolamides and proline were involved, but this did not result in any carrying out in agricultural practice.

The studies of Britikov et al., [C.A. Vol. 66, No. 5, p. 1642, (1965) Fiziol Razt, 12, p. 953–967, (1966) Fiziol Razt, 13, 978–987] using proline or anti-metabolites thereof on male sterility, improved the knowledge in this field without resulting in any practical application.

Artifical technics, such as bees attraction by sugars or like compounds, as described by BURDEN, W.S.P. 4,075,783, do not appear to have reached a noticeable development.

To date, no known techniques or means avoid or reduce floral abortion (non floral pollination due to weather conditions and which might be due to pollen sterility). In the agricultural, horticultural, sylvan, aquacultural fields etc . . . , there is no known process for increasing pollination.

The present invention provides a means for increasing the floral fertility (pollination capacity, particularly under defavourable weather conditions) consisting of applying to the plants, during the period comprised between floral induction and the end of inflorescence, a specific amount of lipoaminoacids and/or related compounds. Specific amount means that quantitites brought by hectare should be comprised between 5 and 100 g and applied under the form of foliar sprayings of solutions or of aqueous suspensions, wherein lipoaminoacids or related compounds concentrations are comprised between 10 and 1000 ppm.

The aim of the present invention is to improve the quality of floral material (stamens and pistils). The period of use is after and not before floral induction because the lipoaminoacids and related compounds don't seem to have any effect on floral induction itself but they speed up and enlarge floral process and, consequently, they can be used during all the inflorescence period.

On certain plants, particularly peas, it may be preferably to spray the lipoaminoacids or related compounds right in the middle of the flowering period such that, even if weather conditions do not remain favourable, pollination can be secured up to the end of the cycle, which leads to more abundant and larger pods.

Further to their action against abortion, an increase of 10 to 20% of the fecundated flowers in normal conditions can be expected from lipoaminoacids and related compounds.

Lipoaminoacids and related compounds should be understood as described in Morelle French Pats. Nos. 2,403,024, 2,495,608, 2,503,144 and 2,503,153, the agricultural portions of which have been assigned to the applicant.

The lipoaminoacids and related compounds are, accordingly, acyl aminoacids with an acylating moiety containing from 4 to 30 carbon atoms (either lipomonoaminoacids or polyaminoacids) and their derivatives as salts either formed with metals or with one or more amines, or with basic aminoacids. These compounds may be used alone or associated with other substances, whose action may be advantageous for plants. The term lipoaminoacids as used in the specification and claims means lipoaminoacids and/or related compounds which are defined as the result of acylation by a fatty acid comprising from 4 to 30 carbon atoms of either isolated naturally occurring amino acids (lipomonoaminoacids) or mixtures of naturally occurring amino acids obtained by hydrolysis of proteins (lipopolyaminoacids) and as the salts of the same with metals or with one or more amines or with basic amino acids.

According to the invention, it has been found that, for each plant and each selected lipoaminoacid, there are accurate ranges both for the amounts to be used by hectare and for the concentrations of solutions or of aqueous suspensions applied. For instance, butyrylcollagen acid on corn, in order to increase the pollination and consequently the number of grains, must be brought preferably by foliar sprayings, from the first appearance of stamens, with around 20 g by hectare in 200 l of water, i.e. at a concentration of 100 ppm. Broadly, the amount of lipoaminoacids to be applied to the plants ranges between 5 to 50 g per hectare at concentrations between 10 to 1000 ppm.

In these conditions, the increase of output can reach 10 or 15 quintals by hectare, but the results are different according to varieties of corn used; they are better with Pernel, Arminda or Normal than with Camp Remy.

The close relationship between the results and the varieties is, itself, dependent upon the weather conditions of the year; the experiments show that the fecundating action of lipoaminoacids leads to a result close to the maximum of the variety involved but that it does not effect the level of this maximum. The action on outputs, if it is closely related with the number of fecundated grains or berries, is also dependent upon the level of general fertilization by fertilizers and oligo-elements. For instance, the action of butyrylcollagenic acid on floral pollination can lead to a supplementary output only if fertilization meets the needs of the plant.

On vines which are sensitive to abortion, and particularly grenache, merlot, pinot noir and chardonnay, the increase of output may frequently be of some thousand kilos of grapes by hectare when using butyrylcollagen in amounts and concentrations conditions similar to these used on corn.

The acyl aminoacids, whose acylating moiety comprises less than 12 carbon atoms, have to be used in amounts by hectare comprised between 5 and 50 g and, preferably, sprayed under the form of solutions or aqueous suspensions, wherein the concentrations in lipoaminoacids are comprised between 10 and 1000 ppm. The doses have to be increased to 25–100 g when lipoaminoacids have an acylating moiety comprising more than 12 carbon atoms (corresponding concentrations 50 to 10 000 ppm).

The amounts and concentrations have to be adapted to the nature of plants, to the varieties or to the conditions of culture but the indicated ranges are usually suitable for cereals, rice, maize, sunflower, peas, beans, vines, fruit-trees etc . . .

The foliar spraying may be applied at the apparition of the first floral buds, on a vine for instance. The application may be renewed 8 days layer, should the flowering process not be achieved, due to bad weather conditions.

To sum up, the process consists of applying lipoaminoacids, i.e. acyl aminoacids with an acylating moiety containing from 4 to 30 carbon atoms (either lipomonoaminoacids or polyaminoacids), i.e. the mixture obtained by acylation, by the selected acylating moiety, of a mixture of naturally occuring aminoacids obtained by hydrolysis of proteins, and their derivatives as salts either formed with metals or wtih one or more amines, or with basic aminoacids, preferably by foliar sprayings, in order to speed up and enlarge floral process; this application has to be made during inflorescence, with well defined amounts by hectare and concentrations of the solutions or suspensions in water.

It will be noted that Morelle's U.S. Pats. Nos. 2,503,144 and No. 2,503,153 of Apr. 2 1981 don't describe or claim any action regarding flowering, which is the consequence of a particular metabolic process and that U.S. Pat. No. 2,403,024 of 1977 only claims germination, growth, antifungic and antiparasitic effects, without any reference to flowering ; that is induced by a very specific metabolism. The total pollination depends on the pollen potential, which is increased in the mentioned conditions of use.

Examples of preparation for increasing the floral fertility (a) copper butyryl collagenate 0.012% ethanolamine lauroyl collagenate 0.006% water (b) butyryl collagenic acid 0.006% fatty polyoxyethylen alcohol 0.003% water (c) copper caprylylkeratinate 0.08% ethanolamine lauroyl collagenate 0.04% water (d) copper caprylylglycinate 0.08% ethanolamine lauroyl collagenate 0.04% water (e) butyrylproline 0.003% water (f) butyrylhydroxyproline 0.003% water N.B.: Butyryl collagenic acid should be understood as the result of the acylation by butyric acid of the mixture of aminoacids obtained by the hydrolysis of collagen. Salts of this acid may be obtained, for instance, with copper and ethanolamine. The same remark applies also to caprylylkeratinate and lauroyl collagenate.

I claim:

1. Process for increasing the floral fertility of plants consisting of the step of applying to the plants, during the period betewen floral induction and the end of inflorescence of said plants, a floral fertility increasing amount of lipoaminoacids, said lipoaminoacids being defined as the result of acylation by a fatty acid comprising from 4 to 30 carbon atoms of a compound selected from the group consisting of isolated naturally occuring aminoacids, mixtures of naturally occuring aminoacids obtained by hydrolysis of proteins, metal or amine salts of either of the foregoing, and basic aminoacids, thereby increasing the floral fertility of the plant.

2. The process of claim 1, wherein the lipoaminoacids are applied to the plants in amounts between 5 and 100 g per hectare, said lipoaminoacids applied in the form of suspensions or solutions in water, at concentrations between 10 and 1000 ppm.

3. The process of claim 2, wherein the acylating fatty acid moiety comprises from 4 to 12 carbon atoms and the lipoaminoacids are applied at amounts of 5 to 50 g per hectare at concentrations between 10 to 1000 ppm.

4. The process of claim 2, wherein the acylating fatty acid moiety comprises more than 12 carbon atoms and the lipoaminoacids are applied at amounts of 25 to 100 g per hectare at concentrations between 50 to 10,000 ppm.

5. The process of claim 3, wherein the lipoaminoacids are butyryl collagenic acids or salts thereof at a total concentration between 50 and 200 ppm.

* * * * *